US008969833B1

(12) United States Patent
Gongora et al.

(10) Patent No.: US 8,969,833 B1
(45) Date of Patent: Mar. 3, 2015

(54) METHOD AND SYSTEM FOR PERCEIVING A BOUNDARY BETWEEN A FIRST REGION AND A SECOND REGION OF A SUPERABRASIVE VOLUME (71) Applicant: US Synthetic Corporation, Orem, UT (US)

(72) Inventors: Giovani J. Gongora, Provo, UT (US); Michael A. Vail, Genola, UT (US)

(73) Assignee: US Synthetic Corporation, Orem, UT (US)

( * ) Notice: Subject to any disclaimer, the term of this patent is extended or adjusted under 35 U.S.C. 154(b) by 97 days.

(21) Appl. No.: 13/714,758

(22) Filed: Dec. 14, 2012

Related U.S. Application Data (60) Provisional application No. 61/576,823, filed on Dec. 16, 2011.

(51) Int. Cl.
G01N 21/64 (2006.01)
G01N 23/22 (2006.01)
(52) U.S. Cl.
CPC ..................................... G01N 23/22 (2013.01)
USPC ....................................................... 250/459.1
(58) Field of Classification Search
CPC ..................................................... G01N 23/203
USPC ....................................................... 250/459.1
See application file for complete search history.

(56) References Cited

U.S. PATENT DOCUMENTS

| 2,895,888 A | 7/1959 | Varner |
| 3,271,572 A | 9/1966 | Lieber et al. |
| 3,364,354 A | 1/1968 | Fries |
| 3,435,668 A | 4/1969 | Sandwith |

(Continued)

FOREIGN PATENT DOCUMENTS

| DE | 0152202 | 11/1981 |
| GB | 614396 A | 12/1948 |

(Continued)

OTHER PUBLICATIONS

T. Wroblewski, "X-Ray imaging of polycrystalline and amorphous materials" JCPDS—International Centre for Diffraction Data, 1997.

(Continued)

Primary Examiner — Kiho Kim
(74) Attorney, Agent, or Firm — Holland & Hart, LLP (57) ABSTRACT Methods of evaluating a superabrasive volume or a superabrasive compact are disclosed. One method may comprise exposing a superabrasive volume to radiation and detecting a response of the radiation when it interacts with the superabrasive volume. In one embodiment, a boundary may be perceived between a first region and a second region of the superabrasive volume in response to detecting the response of the radiation. In one particular embodiment, a boundary between a catalyst-containing region and a catalyst-diminished region of a polycrystalline diamond volume may be perceived. Additionally, a depth to which a catalyst-diminished region extends within a polycrystalline diamond volume of a polycrystalline diamond compact may be measured based on the monitored response of the radiation. In a further embodiment, a non-planar boundary between the two regions may be mapped. A system configured to evaluate a superabrasive volume is also disclosed.

18 Claims, 2 Drawing Sheets

(56) References Cited

U.S. PATENT DOCUMENTS

| | | | |
|---|---|---|---|
| 3,519,824 | A | 7/1970 | Weinstock et al. |
| 3,720,833 | A | 3/1973 | Hay |
| 3,745,623 | A | 7/1973 | Wentorf, Jr. et al. |
| 3,769,511 | A | 10/1973 | Delacy |
| 4,079,237 | A | 3/1978 | Schlesinger |
| 4,089,054 | A | 5/1978 | Ott |
| 4,155,009 | A | 5/1979 | Lieber et al. |
| 4,224,380 | A | 9/1980 | Bovenkerk et al. |
| 4,406,948 | A | 9/1983 | Fischer et al. |
| 4,437,012 | A | 3/1984 | Cavy et al. |
| 4,441,022 | A | 4/1984 | Joffe et al. |
| 4,450,724 | A | 5/1984 | Cheney et al. |
| 4,466,945 | A | 8/1984 | Cheney |
| 4,467,198 | A | 8/1984 | Joffe et al. |
| 4,470,956 | A | 9/1984 | Cheney et al. |
| 4,832,708 | A | 5/1989 | Csillag |
| 5,119,540 | A | 6/1992 | Kong et al. |
| 5,139,372 | A | 8/1992 | Tanabe |
| 5,441,817 | A | 8/1995 | Rai |
| 5,469,927 | A | 11/1995 | Griffin |
| 5,583,343 | A | 12/1996 | Dilmanian et al. |
| 5,585,176 | A | 12/1996 | Grab et al. |
| 5,607,489 | A | 3/1997 | Li |
| 5,648,119 | A | 7/1997 | Grab et al. |
| 5,787,145 | A | 7/1998 | Geus |
| 5,930,586 | A | 7/1999 | Jain et al. |
| 6,029,502 | A | 2/2000 | Stuker |
| 6,040,198 | A | 3/2000 | Komiya et al. |
| 6,287,682 | B1 | 9/2001 | Grab et al. |
| 6,344,149 | B1 | 2/2002 | Oles |
| 6,363,787 | B1 | 4/2002 | Carlson et al. |
| 6,517,902 | B2 | 2/2003 | Drake et al. |
| 6,544,308 | B2 | 4/2003 | Griffin |
| 6,585,064 | B2 | 7/2003 | Griffin et al. |
| 6,589,640 | B2 | 7/2003 | Griffin et al. |
| 6,592,985 | B2 | 7/2003 | Griffin et al. |
| 6,630,363 | B2 | 10/2003 | Koveshnikov |
| 6,739,214 | B2 | 5/2004 | Griffin et al. |
| 6,749,033 | B2 | 6/2004 | Griffin et al. |
| 6,797,326 | B2 | 9/2004 | Griffin et al. |
| 6,829,328 | B2 | 12/2004 | Kim et al. |
| 6,892,940 | B2 | 5/2005 | Kocarev et al. |
| 6,946,394 | B2 | 9/2005 | Fielden et al. |
| 7,128,974 | B2 | 10/2006 | Scarsbrook et al. |
| 7,155,963 | B2 | 1/2007 | Nishioka et al. |
| 7,183,547 | B2 | 2/2007 | Yun et al. |
| 7,375,154 | B2 | 5/2008 | Stafford et al. |
| 7,407,012 | B2 | 8/2008 | Keshavan et al. |
| 7,516,804 | B2 | 4/2009 | Vail |
| 7,558,369 | B1 | 7/2009 | Mourik et al. |
| 7,635,035 | B1 | 12/2009 | Bertagnolli |
| 7,681,669 | B2 | 3/2010 | Cannon et al. |
| 7,864,919 | B1 | 1/2011 | Eyre et al. |
| 7,866,418 | B2 | 1/2011 | Bertagnolli et al. |
| 7,981,293 | B2 | 7/2011 | Powell |
| 8,236,074 | B1 | 8/2012 | Bertagnolli et al. |
| 8,596,387 | B1 | 12/2013 | Sani et al. |
| 2005/0241239 | A1 | 11/2005 | Sung |
| 2006/0288756 | A1 | 12/2006 | De Meurechy |
| 2008/0206576 | A1 | 8/2008 | Qian et al. |
| 2009/0139150 | A1 | 6/2009 | Ras |
| 2010/0326741 | A1 | 12/2010 | Patel |
| 2012/0279139 | A1* | 11/2012 | Vedantham et al. ............ 51/298 |

FOREIGN PATENT DOCUMENTS

| | | |
|---|---|---|
| GB | 1473664 A | 5/1977 |
| GB | 2169480 A | 7/1986 |
| JP | 59219500 | 12/1984 |
| JP | 07307370 A | 11/1995 |
| JP | 11258186 A | 9/1999 |
| SU | 665208 | 11/1976 |

OTHER PUBLICATIONS

Shilin et al., A Study on Interfacial Microstructure and Reaction of Polycrystalline Diamond Compacts, Mining and Metallurgical Engineering, vol. 23, No. 6, Dec. 2003.

Semiconductor Fabrication: Technology and Metrology, American Society for Testing and Materials, 1989.

de Boer, "Glancing-incidence x-ray fluorescence of layered materials," Physical Review, vol. 44, No. 2, Jul. 1991, pp. 498-511.

Kane, "Prevent Corrosion of Advanced Ceramics," Chemical Engineering Progress, Jun. 1991, pp. 77-81.

D'Arco et al., "Fluorescence spectra of Eu3+ in synthetic polycrystalline anorthite: Distribution of Eu3+ in the structure," American Mineralogist, vol. 74, pp. 191-199, 1989.

"Measurement of Hard Material Coatings," Helmut Fischer GmbH, Feb. 2003.

Deng et al., "Interfacial Structure, Properties and Bonding Mechanism of 25 mm-Diameter Polycrystalline Diamond Composites," Acta Materiae Compositae Sinica, vol. 21, No. 5, Oct. 2004.

Deng et al., "Diffusion and Infiltration Mechanisms of Cobalt through Diamond Layer during the Sintering of Polycrystalline Diamond Compacts," Chinese Journal of High Pressure Physics, vol. 18, No. 1, Mar. 2004.

Hanyu, et al., "Development of high performance diamond-coated drills for cutting high silicon aluminum alloy," Thin Solid Films 313 (2002) pp. 139-146.

EDAX Focus, "Attaining High Count Rates and X-ray Mapping with the SDD," 2007, pp. 4-5.

EDAX Focus, "Eagle Micro X-ray Fluorescence Analysis of Polycrystalline Diamond Compacts," 2007, p. 3.

Kuang et al., "Study on the Interfacial Morphology and Structure of Diamond Tin Film-Cemented Carbide Substrate," Acta Metallurgica Sinica, vol. 34, No. 7, Jul. 1998.

EDAX Press Release, "Ametek Instruments Help CSI: Miami Solve the Mystery" Jun. 10, 2005.

Biernat, Jr., "Coatings can greatly enhance carbide tool life and performance, but only if they stay in place," Carbide Coatability, vol. 47, No. 2, Mar. 1995.

Adams, "X-ray Fluorescence Measures Coating Thickness," Quality Magazine, May 5, 2003.

R. Klockenkamper et al., "Comparison of Shallow Depth Profiles of Cobalt-implanted Si Wafers Determined by Total Reflection X-ray Fluorescence Analysis after Repeated Stratified Etching and by Rutherford Backscattering Spectrometry," Surf. Interface Anal 27, pp. 1003-1008, 1999.

Human et al., "Electrochemical behaviour of tungsten-carbide hardmetals," Materials Science & Engineering, A209, 1996, pp. 180-191.

Ma et al., "Effects of Implant Copper Layer on Diamond Film Deposition on Cemented Carbides," Plasma Science &Technology, vol. 3, No. 1, 2001, pp. 647-651.

Heimann et al., "X-ray Fluorescence Analysis of CVD-Diamond Coated Substrates in the Scanning Electron Microscope," Practical Metallography, vol. XL, Mar. 2003, pp. 130-138.

Roberts et al., "Nondestructive depth profile measurement of a Co/Ti bilayer using refracted x-ray fluorescence," Appl. Phys. Lett. 66 (16), Apr. 17, 1995, pp. 2054-2056.

Deng et al., "Diffusion and Infiltration Process of Cobalt through Diamond Layer during the Sintering of Polycrystalline Diamond Compact," Journal of Synthetic Crystals vol. 32, No. 4, Aug. 2003.

Souza, et al., "Corrosion and erosion damage mechanisms during erosion-corrosion of WC—Co—Cr cermet coatings," Wear 255 (2003) pp. 146-156.

Kanicky et al., "Analysis of tungsten carbide coatings by UV laser ablation inductively coupled plasma atomic emission spectrometry," Spectrochimica Acta Part B 55 (2000), pp. 575-586.

Cho et al., "The Effect of Several Factors on the Amount of Leached Binder by Electrolysis in Wc—Co Alloy," J. Kor. Inst. Met. & Mater. vol. 37 No. 8 (1991) pp. 973-979.

Zhang et al., "Fabrication and application of chemical vapor deposition diamond-coated drawing dies," Diamond and Related Materials 10 (2001) pp. 33-38.

(56) References Cited

OTHER PUBLICATIONS

Zhibin et al., "Effects of copper implant layers on the adhesion of diamond films on WC—Co substrates," J. Wuhan Inst. Chem. Tech. vol. 22 No. 4, Dec. 2000, pp. 34-36.

Harris et al., "Wear of metal-containing diamond-like carbon coatings," Chemistry and Materials Science, vol. 2, No. 4, pp. 375-380 (abstract only).

Tongson et al., "Surface analysis of WC/Co composite materials (2) Quantitative Auger electron spectrometry," Journal of Vacuum Science and Technology, May 1978, vol. 15, Issue 3, pp. 1133-1138 (abstract only).

Katsumura et al., "Effects of Cobalt Content and Surface State of Substrate on Cutting Performance of Diamond Deposited Cemented Carbide Tool for Al-18% Si Alloy," Sep. 1989, 5 pages. (Journal information unknown) (abstract only).

Piippanen et al., "Determination of cobalt, copper, iron, nickel and zinc in cemented tungsten carbides with cobalt as a binder by FAAS: Matrix effect control by multivariate technique," Journal of Analytical Chemistry, May 1996, vol. 358, Nos. 7-8, pp. 771-774. (abstract only).

Patent No. IP 127570D entitled "Non-destructive technique to quantify cobalt depletion in PCD".

"Analysis of Cobalt, Tantalum, Titanium, Vanadium and Chromium in Tungsten Carbide by Inductively Coupled Plasma-Optical Emission Spectrometry," University of Pretoria, Mar. 2004.

Zhibin et al., "Adhesion improvement of diamond films on cemented carbides with copper implant layer," Thin Solid Films, Jun. 30, 2001, pp. 104-106.

U.S. Appl. No. 13/100,388, filed May 4, 2011.

Edtmaier et. al., "Selective removal of the cobalt binder in WC/Co based hardmetal scraps by acetic acid leaching," Hydrometallurgy, vol. 76, Issues 1-2, Jan. 2005, pp. 63-71 (abstract only).

* cited by examiner

METHOD AND SYSTEM FOR PERCEIVING A BOUNDARY BETWEEN A FIRST REGION AND A SECOND REGION OF A SUPERABRASIVE VOLUME

CROSS-REFERENCE TO RELATED APPLICATIONS

This application claims the benefit of U.S. Provisional Patent Application No. 61/576,823, entitled METHOD AND SYSTEM FOR PERCEIVING A BOUNDARY BETWEEN A FIRST REGION AND A SECOND REGION OF A SUPERABRASIVE VOLUME, filed on Dec. 16, 2011, the disclosure of which is incorporated by reference herein in its entirety.

BACKGROUND

Superabrasive compacts are utilized for a variety of applications and in a corresponding variety of mechanical systems. Such superabrasive compacts may be known in the art, for example, as inserts, buttons, machining tools, wear elements, or bearing elements and may be conventionally manufactured by forming a superabrasive layer on the end of a substrate (e.g., a sintered or cemented tungsten carbide substrate). As an example, polycrystalline diamond, or other suitable superabrasive material, such as cubic boron nitride, may be sintered onto the surface of a cemented carbide substrate under an ultra-high pressure and ultra-high temperature ("HPHT") process to form a superabrasive compact, as described in greater detail below. Polycrystalline diamond elements are used in drilling tools (e.g., inserts, cutting elements, gage trimmers, etc.), machining equipment, bearing apparatuses, wire drawing machinery, and in other mechanical systems. For instance, polycrystalline diamond compacts (PDCs) have found utility as cutting elements in drill bits (e.g., roller cone drill bits and fixed cutter drill bits).

Such PDCs conventionally include a diamond layer or table formed by a sintering process employing HPHT conditions that causes the diamond table to become bonded or affixed to a substrate (such as cemented tungsten carbide substrate), as described in greater detail below. Optionally, the substrate may be brazed or otherwise joined to an attachment member such as a stud or to a cylindrical backing, if desired. Generally, a rotary drill bit may include a plurality of polycrystalline abrasive cutting elements affixed to the drill bit body. Each PDC may be employed as a subterranean cutting element mounted to a drill bit either by press-fitting, brazing, or otherwise coupling a stud to a recess defined by the drill bit, or by brazing the cutting element directly into a preformed pocket, socket, or other receptacle formed in the subterranean drill bit. In one example, cutter pockets may be formed in the face of a matrix-type bit comprising tungsten carbide particles that are infiltrated or cast with a binder (e.g., a copper-based binder), as known in the art. Such subterranean drill bits are typically used for rock drilling and for other operations which require high abrasion resistance or wear resistance.

A PDC is conventionally fabricated by placing a cemented carbide substrate into a container or cartridge with a layer of diamond crystals or grains positioned adjacent one surface of a substrate. A number of such cartridges may be typically loaded into an ultra-high pressure press. The substrates and adjacent diamond crystal layers are then sintered under HPHT conditions. The HPHT conditions cause the diamond crystals or grains to bond to one another to form polycrystalline diamond. In addition, as known in the art, a catalyst may be employed for facilitating formation of polycrystalline diamond. In one example, a so-called "solvent catalyst" may be employed for facilitating the formation of polycrystalline diamond. For example, cobalt, nickel, and iron are among examples of solvent catalysts for forming polycrystalline diamond. In one configuration, during sintering, a solvent catalyst comprising the substrate body (e.g., cobalt from a cobalt-cemented tungsten carbide substrate) becomes liquid and sweeps from the region adjacent to the diamond powder and into the diamond grains. Of course, a solvent catalyst may be mixed with the diamond powder prior to sintering, if desired. Also, as known in the art, such a solvent catalyst may dissolve carbon. Such carbon may be dissolved from the diamond grains or portions of the diamond grains that graphitize due to the high temperatures of sintering. When the solvent catalyst is cooled, the carbon held in solution may precipitate or otherwise be expelled from the solvent catalyst and may facilitate formation of diamond bonds between abutting or adjacent diamond grains. Thus, diamond grains become mutually bonded to form a polycrystalline diamond table upon the substrate. A conventional process for forming polycrystalline diamond cutters is disclosed in U.S. Pat. No. 3,745,623 to Wentorf, Jr. et al., the disclosure of which is incorporated herein, in its entirety, by this reference.

Solvent catalyst in the polycrystalline diamond may be detrimental. For instance, because the solvent catalyst exhibits a much higher thermal expansion coefficient than the diamond structure, the presence of such solvent catalyst within the diamond structure is believed to be a factor leading to premature thermal mechanical damage. Accordingly, as the polycrystalline diamond reaches temperatures exceeding 400° Celsius, the differences in thermal expansion coefficients between the diamond and the solvent catalyst may cause diamond bonds to fail. Of course, as the temperature increases, such thermal mechanical damage may be increased. In addition, as the temperature of the polycrystalline diamond layer approaches 750° Celsius, a different damage mechanism may initiate. More specifically, the solvent catalyst may interact with the diamond to cause graphitization of the diamond. Such graphitization is believed to contribute to or cause mechanical damage within the polycrystalline diamond. This phenomenon may be termed "back conversion," meaning conversion of diamond to graphite. Such conversion from diamond to graphite may cause dramatic loss of wear resistance in a polycrystalline diamond compact and may rapidly lead to insert failure. Accordingly, as known in the art, the solvent catalyst in the polycrystalline diamond layer may be at least partially removed from the polycrystalline diamond. For instance, the solvent catalyst may be at least partially removed from the polycrystalline diamond by acid leaching. Optionally, another material may replace the solvent catalyst that has been at least partially removed from the polycrystalline diamond.

Accordingly, a superabrasive volume may include at least two regions with differing constituents. Thus, it may be advantageous to determine or perceive different regions of a superabrasive volume. For instance, such perception may allow for monitoring of (i.e., quality control) relative to superabrasive apparatus manufacturing and processing methods. Thus, it would be advantageous to provide methods and systems for evaluating (e.g., nondestructively) different regions of a superabrasive volume.

SUMMARY

The present invention relates generally to observing interaction between radiation and a superabrasive volume, a superabrasive compact, or a superabrasive article. More particularly, at least one characteristic of a superabrasive volume or layer may be determined by detecting a response of radiation interacting with the superabrasive volume. Further, a boundary may be perceived in response to monitoring the response of the radiation. In one embodiment, a superabrasive may comprise a polycrystalline diamond. Optionally, a catalyst used for forming the polycrystalline diamond volume may be at least partially removed from a region of the polycrystalline diamond volume. In one example, a depth to which a catalyst has been at least partially removed from a region of a superabrasive volume (e.g., a polycrystalline diamond volume) may be measured.

In accordance with one embodiment of the present invention, a method is provided for evaluating a volume of superabrasive material. The method includes exposing the superabrasive material to radiation. A reaction of the radiation is monitored, wherein monitoring the reaction includes monitoring at least one of the group consisting of backscattered radiation and x-ray fluorescence. A location of the boundary between a first region and a second region of the superabrasive volume is determined in response to the monitored reaction of the radiation, wherein the location of the boundary is approximately 500 µm or greater from a working surface of the volume superabrasive material.

In accordance with another embodiment, another method of evaluating a volume of superabrasive material is provided. The method includes exposing the superabrasive material to radiation and monitoring a reaction of the radiation to which the superabrasive table is exposed. A non-planar boundary between a first region and a second region of the superabrasive volume is then mapped in response to the monitored reaction of the radiation.

In accordance with yet another embodiment, another method of evaluating a volume of superabrasive material is provided. The method includes exposing the superabrasive material to radiation and monitoring a reaction of the radiation to which the superabrasive table is exposed. A location of a boundary between a first region of the superabrasive volume containing a solvent-metal catalyst material and a second region of the superabrasive volume containing a copper material is determined in response to the monitored reaction of the radiation.

In accordance with a further embodiment of the invention, yet another method of evaluating a volume of superabrasive material is provided. The method includes exposing the superabrasive material to radiation and monitoring a reaction of the radiation to which the superabrasive table is exposed. A location of a boundary between a first region of the superabrasive volume containing a solvent-metal catalyst material and a second region of the superabrasive volume containing a carbide material is determined in response to the monitored reaction of the radiation.

Features from any of the various embodiments described herein may be used in combination with one another, without limitation. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Further features of the subject matter of the instant disclosure, its nature, and various advantages will be more apparent from the following detailed description and the accompanying drawings, which illustrate various exemplary embodiments, are representations, and are not necessarily drawn to scale, wherein.

DETAILED DESCRIPTION

The present invention relates generally to characterizing a volume of superabrasive material. Generally, a superabrasive volume may include two or more different regions. For example, a superabrasive volume may be formed by a HPHT sintering process wherein the resulting structure includes different regions of differing composition. In another embodiment, a superabrasive volume may be formed by a HPHT process and may be subsequently treated to remove at least one constituent (e.g., a catalyst) from a selected region of the superabrasive volume. In a further embodiment, another material may replace the removed material (e.g., the removed catalyst).

Various embodiments of the present invention include observing interaction between emitted radiation and a superabrasive volume to perceive a boundary between two regions within the superabrasive volume. One form of radiation includes the emission of beta particles. The phrase "beta particles," as used herein, refers to electrons emitted by unstable atomic nuclei in response to neutron decay (e.g., where a neutron decays into a proton and an electron). As known in the art, beta particles (which may also be referred to as beta radiation) may comprise positrons (i.e., so-called "antielectrons" which are identical to electrons but carry a positive electrical charge). Accordingly, beta particles are positrons which may be emitted from radioisotopes. X-ray radiation and other forms of radiation may also be utilized as discussed hereinbelow.

The present invention contemplates that if radiation interacts with a superabrasive volume, a response to that interaction of the radiation with the superabrasive volume may be detected. An appropriate detector may be employed to monitor or measure the response of the radiation interacting with the superabrasive volume in order to perceive a boundary between a first region of the superabrasive volume and a second region of a superabrasive volume. The term "superabrasive," as used herein, refers to any material having a hardness that is at least equal to a hardness of tungsten carbide. For example, polycrystalline diamond and cubic boron nitride are each a superabrasive material.

Various improvements in materials and manufacturing processes have yielded new constructions from superabrasive materials having improved performance characteristics (e.g., wear resistance, toughness and thermal stability). The new constructions may exhibit, for example, a different percentage of catalyst material in the resulting structure. They may also exhibit a different diamond density or include materials in the final structure that weren't previously contemplated.

For example, so-called two step processes of forming PCD compacts have been developed, wherein a superabrasive table is formed through a HPHT process using a metal solvent catalyst material. The catalyst material may then be removed from the superabrasive table, either partially or substantially wholly removed, such as by a leaching process. The "pre-sintered" superabrasive table may then be positioned against a substrate and subjected to another HPHT process to join the substrate and the table, wherein an infiltrant material infiltrates interstitial regions of the at least partially leached superabrasive table. An example of a two-step process is set forth in U.S. patent application Ser. No. 11/545,929, filed on Oct. 10, 2006, and entitled SUPERABRASIVE ELEMENTS, METHODS OF MANUFACTURING, AND DRILL BITS INCLUDING SAME, the disclosure of which is incorporated by reference herein in its entirety. Another related example is described in U.S. patent application Ser. No. 13/100,388, filed May 4, 2011, and entitled POLYCRYSTALLINE DIAMOND COMPACT INCLUDING A POLYCRYSTALLINE DIAMOND TABLE CONTAINING ALUMINUM CARBIDE THEREIN AND APPLICATIONS THEREFORE, the disclosure of which is incorporated by reference herein in its entirety.

Yet another example of such a process is disclosed in U.S. patent application Ser. No. 12/898,047, filed on Oct. 5, 2010, an entitled POLYCRYSTALLINE DIAMOND COMPACT INCLUDING A NON-UNIFORMLY LEACHED POLYCRYSTALLINE DIAMOND TABLE AND APPLICATIONS THEREFOR, the disclosure of which is incorporated by reference herein in its entirety. This same application additionally discloses a superabrasive table having a region where catalyst material is removed, the bounds and geometry of the catalyst-diminished region being tailored such that the depth of the region can vary from one location to another as that depth is measured from a working surface (e.g., from an upper surface or from a lateral side surface) in a direction substantially perpendicular to a plane that is tangent to a point on the surface. U.S. Pat. No. 7,681,669 to Cannon et al., the disclosure of which is incorporated by reference in its entirety, also describes various superabrasive volumes having geometrically tailored catalyst-diminished regions.

In addition to the varied thickness of a leached or catalyst-diminished region, new processes of forming superabrasive tables may result in leaching depths that are greater than in conventionally formed superabrasive tables. For example, in some configurations, a superabrasive table may exhibit a region adjacent a working surface that is substantially devoid of catalyst material up to a depth of 500 micrometers (μm) or greater. In another embodiment, such a depth may be as great as 600 μm. In yet another embodiment, such a depth may be as great as 700 μm or greater. Again, as noted above, such a depth may also vary relative to a defined surface.

Another improvement in superabrasive structures includes providing a material other than a conventional metal-solvent catalyst in a region adjacent the working surface of the structure. For example, a non-metal catalyst material may be disposed in the interstices of a region adjacent the working surface. In another embodiment, copper, or a copper alloy (e.g. a copper-tin alloy), may be disposed in the interstices of a region adjacent a working surface. Examples of such embodiments are described, for example, in U.S. Pat. No. 7,635,035 to Bertagnolli et al., the disclosure of which is incorporated by reference herein in its entirety. Other materials may also be disposed in a region adjacent the working surface (e.g., replacing a catalyst material that has been removed from such a region). For example, a carbide material may be disposed in such a region among the interstices of, for example, a polycrystalline diamond material. Such carbide materials may include, for example, titanium carbide, zirconium carbide, hafnium carbide, vanadium carbide, niobium carbide, molybdenum carbide and tungsten carbide.

Another example of an improved superabrasive structure is set forth in U.S. Pat. No. 7,866,418 to Bertagnolli et al., the disclosure of which is incorporated by reference herein, in its entirety. U.S. Pat. No. 7,866,418 discloses polycrystalline diamond cutting elements (and methods for making such) that are formed to have a reduced content of catalytic material, a coercivity of about 115 Oesrstads (Oe) or greater and a specific magnetic saturation of about 15 Guass·cm$^3$/gram (G·cm$^3$/g).

These various methods of making superabrasive tables, and the resulting constructions, present various difficulties in quality assurance including non-destructive means of verifying certain characteristics of the resulting structures. For example, many known methods of determining the depth of a specified region adjacent a working surface (such as a leached depth or of a catalyst-diminished region may be limited with respect to the depths they are able to discern and, thus, may not able to determine depths such as 500 μm or greater.

Some examples of known methods for determining leached depths include those described by U.S. Pat. No. 7,864,919 to Eyre et al., the disclosure of which is incorporated by reference herein in its entirety. The Eyre patent describes the use of x-ray fluorescence in determining the depth of a leached or catalyst-devoid region (as measured from a defined working surface) of a conventional polycrystalline body by using x-rays to excite a target atom and emit x-ray fluorescence. The target atom is associated with a second region, such as a region containing a catalyst material. Indeed, in the embodiments described by the Eyre patent, the target atom is an atom of the catalyst material. The emitted fluorescence is detected and the location of the target atom is determined. The location of the target atom is then associated with the depth of a leached region. However, there is no description set forth in the Eyre patent regarding the determination of extended depths of such a leached or catalyst devoid region (i.e., 500 μm or greater as measured from a defined working surface). Nor is there any description in the Eyre patent of the efficacy of such a method when used in conjunction with superabrasive tables having different materials disposed in the region adjacent a working surface (e.g., copper, carbides, etc.) or when used with superabrasive tables that have been specifically tailored to exhibit desired material characteristics, such as set forth in U.S. Pat. No. 7,866,418.

Another example of a method for determining leached depths is described in U.S. Pat. No. 7,558,369 to Mourik et al., the disclosure of which is incorporated by reference herein. The Mourik patent describes the use of x-ray radiation to obtain a profile image of a polycrystalline diamond compact. The radiation is applied to the side of the compact, passes through the compact and is received by a detector to provide the profile image. In essence, an x-ray image is taken of the compact from a side or elevational point of view. It is noted that there are some limitations to using such an approach such as, for example, the inability to obtain useful information regarding the depth of a region (e.g., a catalyst diminished region) that varies in a direction that is substantially parallel to that of the radiation passing through the compact. Such a variation in depth would be difficult to determine based on the profile approach described by the Mourik patent.

The present invention provides a means of perceiving or determining a boundary between two regions of a superabrasive material including regions having any of a variety of material compositions, regions with nonplanar boundaries therebetween, and regions having extended depths relative to a working surface. In one embodiment, the superabrasive material may include a coherent matrix of a first material extending through both regions, while the first region includes a second material disposed within the interstices of the matrix material and the second region is substantially devoid of the second material. The second region may be substantially devoid of any other material (other than the first material), or it may include a third material disposed within the interstices of the matrix material. For example, the first (matrix) material may include polycrystalline diamond, while the second material (disposed within the first region) may include a solvent-metal catalyst such as cobalt. The second region may be substantially devoid of the catalyst material and may or may not include another material different than the material disposed within the first region. The second region may exhibit a depth, as measured from a defined working surface, that is 500 µm or greater. Additionally, a boundary profile or map may be determined for boundaries that vary in depth or location relative to a known surface topography of the superabrasive volume.

Figure 1:
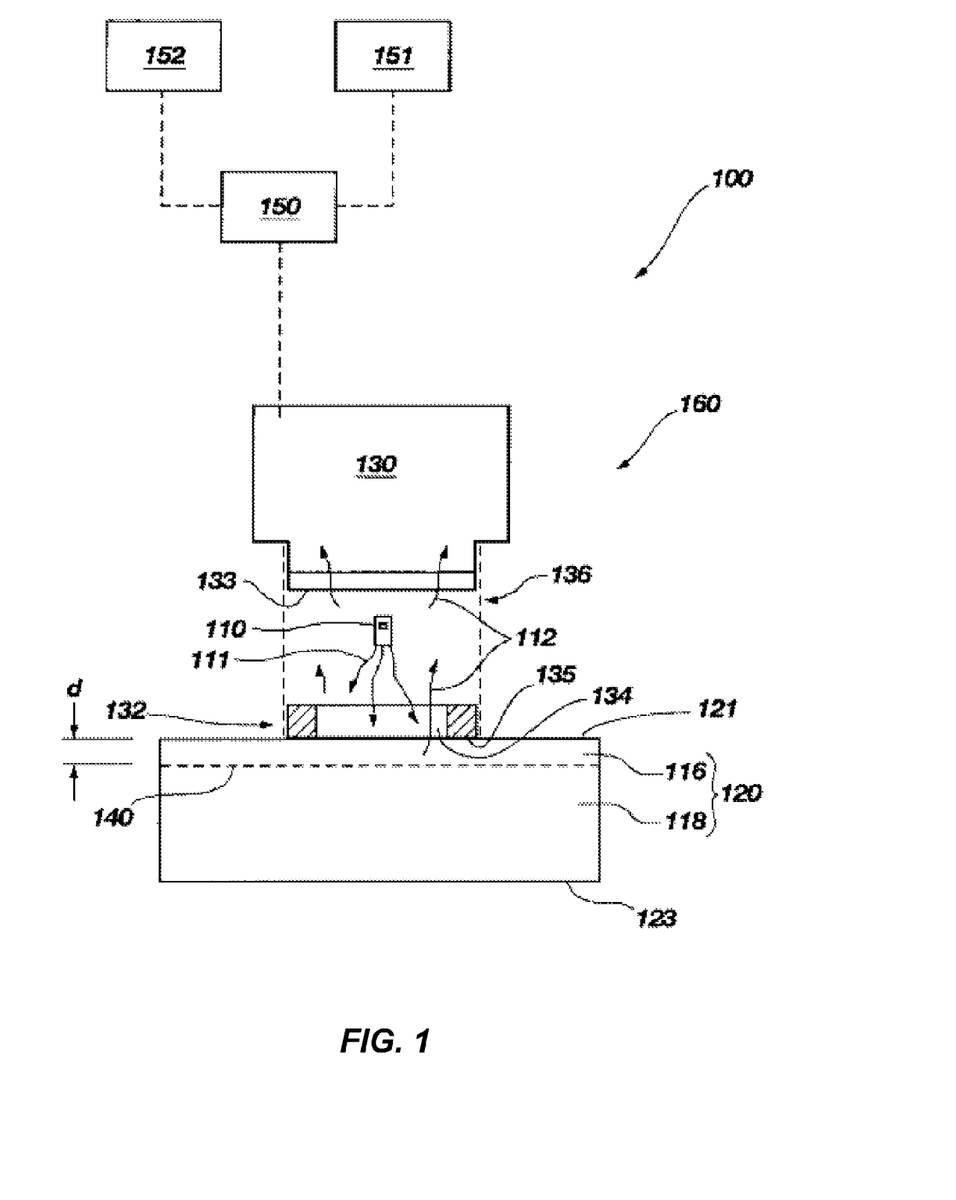
FIG. 1 a schematic, cross-sectional view of an evaluation system during use in evaluating a superabrasive volume.

Referring to FIG. 1, a schematic, cross-sectional representation of an evaluation system 100 is shown. The system 100 comprises a radiation source 110, a detector 130, and an analysis system 150. In one embodiment, the radiation source 110 may comprise a beta particle source, such as thallium (e.g., radioisotope thallium 204). Other materials that emit beta particles, as known in the art, may also be used including, for example, cesium and strontium. Such sources may provide radiation at a low enough level to help ensure safety while exhibiting a relatively long half-life such as with the examples given. In other embodiments, another source of radiation may be used, such as, for example, alpha, gamma or x-ray radiation.

An example of an evaluation system that utilizes a radiation source is set forth in U.S. Pat. No. 7,918,293 to Vail et al., the disclosure of which is incorporated by reference herein in its entirety. In some systems, an x-ray source may be used as a radiation source for use in detecting x-ray fluorescence. In one embodiment, such a system may direct an electron beam at a target material, such as rhodium, at a voltage of approximately 1-50 kilovolts and a current of 1 milliamp to produce radiation having a spot size of approximately 0.1 millimeters to approximately 3 millimeters. In operating the evaluation system 100 with different types of samples (e.g., samples having increased depths to be measured, samples with different materials used as infiltrants, etc.), the voltage of the radiation source may be adjusted in order to change the energy level of the radiation.

The radiation source 110 may be selected or tailored so that the radiation is emitted at a desired energy level. Selectively setting the radiation level (whether it be from a beta particle source, an x-ray source, a gamma ray source, an electron beam source, an ion beam source, or some other radiation source) enables the radiation to interact with an anticipated boundary depending, for example, on the expected depth of the boundary from the working surface, the types of material comprising the different regions of the superabrasive volume, and other variables that may affect the interaction of the radiation with the superabrasive volume 120.

Considering a system where the radiation source 110 emits beta particles, the system 100 may additionally include a metering port 132 positioned at a selected distance relative to radiation source 110. The system 100 may be configured so that the radiation source 110 is directed toward an aperture 134 of metering port 132. Optionally, emitted beta particles 111 emitted from beta particle source 110 may be collimated so that emitted beta particles 111 generally travel within a selected "spot size." Thus, emitted beta particles 111 may optionally pass through the metering port 132 without substantial interaction therewith. In addition, the metering port 132, in combination with a coupling structure 136, may be configured to inhibit, block, or otherwise interfere with transmission of scattered (e.g., reflected, backscattered, or otherwise influenced to change direction or velocity) beta particles 112 except for those passing through aperture 134 of metering port 132 in a suitable direction to pass into the detector 130 through a detector surface 133. In one embodiment wherein the radiation source 110 emits beta particles, the radiation detector 130 may comprise a Geiger-Mueller tube or any other device as known in the art for detecting beta particles. In other embodiments, the detectors may be configured to detect and monitor, for example, x-ray fluorescence, reflected x-rays, diffracted x-rays, reflected radiation, scattered radiation, secondary radiation, or millimeter waves.

In other embodiments, associated components and structures may be likewise used to focus the radiation and monitor any reaction or change in the emitted radiation responsive to the radiation interacting with the superabrasive volume and its various constituents. In another embodiment, when using other radiation sources, the metering port 132 may be configured as some other structure that may be used a benchmark for comparison with radiation that interacts with the superabrasive volume 120.

While not specifically shown in the drawing figures, the radiation source 110 and a table or other structure upon which samples may be placed can be configured to be moveable relative to one another during the analysis process. For example, a table may be configured to move in the X and Y planes relative to the radiation source 110 so that a plurality of a samples may be subjected to radiation in a specified pattern. Thus, in one example, samples may be arranged in rows, columns, or both, and the table or structure on which they are placed may be moved such that each of the samples is subjected to radiation and analyzed.

Still referring to FIG. 1, the analysis system 150 may comprise a computer or another device including at least one processor. Further, at least one input device 151 (e.g., a mouse, a keyboard, etc.) and at least one output device (e.g., a monitor, a printer, a liquid crystal display, etc.) may be operably coupled to the analysis system 150. The analysis system 150 may communicate with the detector 130 to monitor and interpret the information received by the detector. For example, in the case of a radiation source 110 that emits beta particles, the analysis system 150 may be configured to measure a voltage or other signal from the detector 130, based on the backscattered beta particles, to perceive a boundary within a superabrasive volume (e.g., measure a depth of the boundary from an exterior or working surface of the superabrasive volume). In one such embodiment, the analysis system 150 may be configured to determine a quantity of scattered beta particles 112 detected by beta particle detector 130 for a given amount of time.

The analysis system 150 may be configured to correlate the detected reaction of the radiation with the superabrasive volume to a depth "d" between a lower surface 135 of metering port 132 (or other benchmark structure) and a boundary 140 between the two regions 116 and 118 of the superabrasive volume 120. As shown in FIG. 1, the boundary 140 may comprise a boundary surface between region 116 and region 118. As previously discussed, while a continuous coherent matrix (e.g., sintered polycrystalline diamond exhibiting diamond-to-diamond bonds between a plurality of diamond grains) may extend throughout both regions 116 and 118, one region (e.g., region 118) may include a first material among the interstices of the matrix material while the other region (e.g., region 116) may include a different material, or be substantially devoid of any material, among the interstices of the matrix material.

Thus, in one embodiment, during operation, the lower surface 135 of the metering port 132 may be positioned at a known distance from upper surface 121 of superabrasive volume 120. For example, the metering port 132 may be positioned adjacent to or abutting upper surface 121 of superabrasive volume 120. Emitted beta particles 111 may pass through aperture 134 of metering port 132 and may interact with first region 116 of superabrasive volume 120, second region 118 of superabrasive volume 120, or both to perceive boundary 140 (e.g., at least a portion of a boundary surface) between first region 116 and second region 118. In one embodiment, first region 116 of superabrasive volume 120 may exhibit a density (i.e., an average atomic number) which is less than a density (i.e., an average atomic number) of second region 118 of superabrasive volume 120. Such a configuration may cause emitted beta particles 111 to interact with the portion of second region 118 substantially defining the boundary 140. Accordingly, in such a configuration, scattered beta particles 112 may travel toward beta particle detector 130 through aperture 134 of metering port 132. One of ordinary skill in the art will appreciate that as depth d increases, relatively fewer scattered beta particles 112 may be received and detected by beta particle detector 130.

In other embodiments, other types of radiation may similarly be emitted by the radiation source 110 to interact with the first region 116, the second region 118 or both, and possibly some other structure placed at a known position relative to a surface of the superabrasive volume 120, in order to determine the position of the boundary between the two regions 116 and 118.

The analysis system 150 may be calibrated by exposing a superabrasive volume to a known level of radiation, detecting the reaction of the radiation as it interacts with the superabrasive volume, and determining at least one characteristic of a boundary by a different or independent method. For example, in one embodiment, a superabrasive volume may be destructively evaluated to determine a position or another characteristic (e.g., a size, shape, composition, etc.) of a boundary within the superabrasive volume. Specifically, for example, a superabrasive volume may be analyzed via system 100 and then may be sectioned (i.e., cut or otherwise separated into pieces) and analyzed to determine a depth d at which the boundary is positioned. Such a determination may utilize, without limitation, scanning electron microscopy, x-ray diffraction, or any other analytic processes as known in the art. The present invention further contemplates that a plurality of superabrasive volumes each exhibiting a different depth d at which a boundary is positioned may be analyzed via system 100 and also analyzed via a different method to develop calibration data which analysis system 150 may employ to determine or predict a depth d for a given superabrasive volume.

Explaining further, the evaluation system 100, and in particular the analysis system 150, may comprise calibration data for correlating a monitored response to radiation exposure with an indicated depth of boundary between a first region and a second region of a superabrasive volume. For example, considering the embodiment wherein the radiation source emits beta particles, the calibration data may comprise a first measured quantity of scattered beta particles associated with a first depth (e.g., a first depth determined by destructive evaluation of at least one sample or confirmed by other radiation measurements) and at least a second measured quantity of scattered beta particles associated with a second depth (e.g., a second depth determined by destructive evaluation of at least one sample or confirmed by other radiation measurements). The first depth may be relatively shallow, while a second depth may be of a magnitude near an anticipated upper limit. For example, a first depth may be substantially zero (i.e., an exterior surface of a superabrasive volume may be a boundary), or may be between about zero and 0.002 inches. As a further example, a second depth may be about 0.005 inches or greater. In other embodiments, the second depth may be about 0.02 inches (about 500 µm) or greater. In other embodiments, the second depth may be about 0.024 inches (about 600 µm) or greater. In yet other embodiments, the second depth may be about 0.028 inches (about 700 µm) or greater. In another embodiment, the second depth may be about 0.032 inches (about 800 µm) or greater. In a further embodiment, the second depth may be about 0.036 inches (about 900 µm) or greater. In another embodiment, the second depth may be about 0.04 inches (about 1,000 µm) or greater. In another embodiment, the second depth may be between about 0.04 inches (about 1,000 µm) and about 0.06 inches (1,500 µm).

In addition, one of ordinary skill in the art will appreciate that once a first measured or detected quantity of scattered beta particles (or other radiation response) may be correlated to the first depth and a second measured or detected quantity of scattered beta particles (or other radiation response) may be correlated to a second depth. Further, one of ordinary skill in the art will appreciate that linear regression, or other appropriate analysis, may be employed (via the first measured depth, first measured quantity of beta particles, the second measured depth, and the second measured quantity of beta particles) to calculate (predict, calculate, or extrapolate) a depth associated with a measured quantity of scattered beta particles that differs from the first or second measured quantity of scattered beta particles. Any regression or predictive algorithm as known in the art may be employed for predicting or calculating a depth of a region of a superabrasive volume based on a detected or measured quantity of scattered beta particles.

Figure 2:
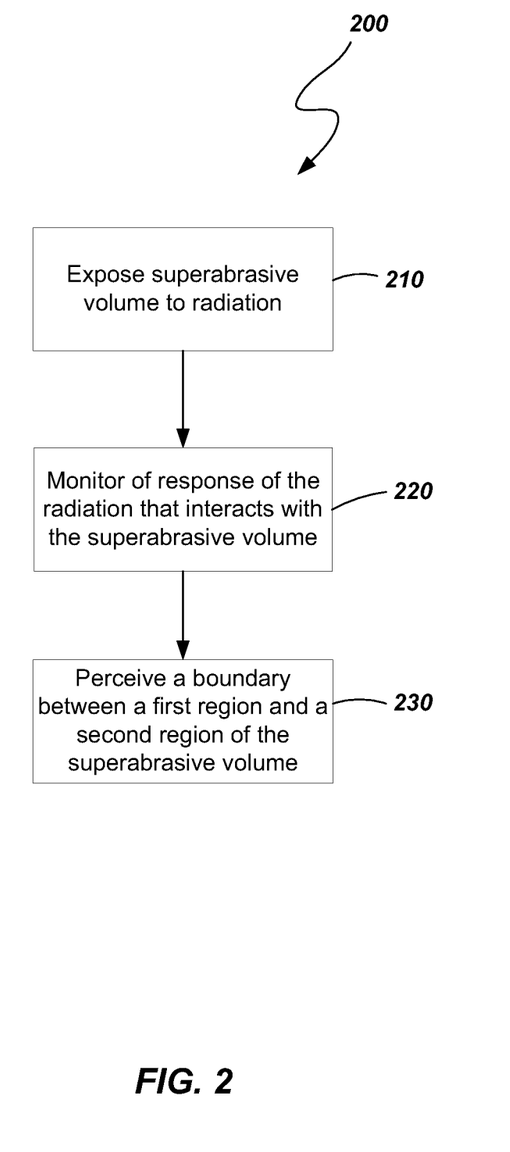
FIG. 2 is a schematic flow chart of a method of evaluating a superabrasive volume in accordance with an embodiment of the present invention.

Referring now to FIG. 2, a schematic flow chart depicts one embodiment of a method 200 of evaluating a superabrasive volume. The method 200 may comprise exposing a superabrasive volume to a radiation source as indicated by reference numeral 210. For example, the superabrasive volume may be exposed to a plurality of beta particles or to x-ray radiation. A response to the interaction of the radiation with the superabrasive is monitored, as indicated at 220. The means of monitoring and determining the response to the radiation will depend, in part, on the type of radiation being used in the method. For example, if the superabrasive volume is exposed to beta particles, the monitoring of the response may include monitoring back scattered particles. In another example, if the superabrasive volume is exposed to x-rays, the monitoring of the response may include monitoring for and detecting x-ray fluorescence that may be induced within a material of the superabrasive volume or it may include detecting and monitoring backscattered x-rays. Of course other means of monitoring and detecting may also be used.

A boundary between a first region of the superabrasive volume and a second region of the superabrasive volume is then perceived based on the monitored response of the interaction of the radiation with the superabrasive volume, as indicated at 230. The boundary may be determined, for example, by comparing the actual, monitored response to calibration data previously obtained or developed such as described above.

In one embodiment, a first region of a superabrasive volume and a second region of the superabrasive volume may differ in composition with a boundary at least partially delineating the first region from the second region. For example, a first region and a second region of a superabrasive volume may include constituents that differ in atomic number. In one particular example, a first region of a superabrasive volume may include at least one constituent exhibiting an atomic number that differs by at least about 20% from an atomic number of at least one constituent of a second region of a superabrasive volume.

As previously noted, in various embodiments, the superabrasive volume may comprise a plurality of super-hard particles or superabrasive grains that are mutually bonded to one another to form a coherent skeleton or matrix structure. For example, a superabrasive volume may comprise polycrystalline diamond, cubic boron nitride, or any other superabrasive as known in the art, without limitation. One of ordinary skill in the art will appreciate that a first region and a second region of a superabrasive volume may be formed by different processes, with different materials, by changing a composition of at least one of the first and second regions, or by combinations or variations of the foregoing.

For example, as explained above, a superabrasive volume may be formed by employing a so-called catalyst which may facilitate grain-to-grain bonding. Further, subsequent to formation of the superabrasive volume in the presence of a catalyst, at least a portion of the catalyst may be removed from a selected region of the coherent skeleton or matrix structure of the superabrasive volume. Thus, a superabrasive volume may comprise a catalyst-containing region and a catalyst-diminished region, wherein a boundary is defined between the regions. Perceiving such a boundary may comprise measuring a depth to which a catalyst (e.g., cobalt, nickel, iron, etc.) has been at least partially removed from a region of the polycrystalline diamond volume.

As mentioned above, a variety of material-related characteristics as well as geometry-related aspects may influence the use of radiation for perceiving a boundary within a superabrasive volume. The present invention contemplates that any superabrasive volume, superabrasive compact, or any other superabrasive article may be evaluated by employing radiation such as beta particles, x-ray radiation or other appropriate radiation sources. For example, the present invention contemplates that a superabrasive compact comprising a superabrasive volume including an arcuate exterior surface may be evaluated. Moreover, a boundary that is non-linear, non-planar, that generally exhibits variation in more than two dimensions, or that varies in its distance from a reference surface (e.g., a working surface, whether planar or nonplanar) of the superabrasive volume, may be mapped to determine the contours of the boundary and confirm whether or not the superabrasive volume has been manufactured according to a desired design. Depending on the type of radiation used, and the means used for detecting a response of the radiation, such a mapping may include taking multiple measurements with the radiation focused on different locations of the superabrasive volume.

One of ordinary skill in the art will understand that any of the above-discussed methods and systems may provide the ability to nondestructively evaluate a superabrasive volume. Thus, characteristics of a superabrasive volume that is evaluated via radiation (e.g., beta particles or x-ray radiation) may be substantially unaffected by interaction with such radiation. Thus, such methods and systems may provide advantage over conventional methods and systems configured for destructive evaluation of superabrasive volumes. Further, although the methods and systems described above have been discussed in the context of superabrasive structures (e.g., comprising polycrystalline diamond), the present invention is not so limited, and one of ordinary skill in the art will appreciate that the discussed methods and structures could be used for varied applications as known in the art, without limitation. In addition, while certain embodiments and details have been included herein for purposes of illustrating aspects of the instant disclosure, it will be apparent to those skilled in the art that various changes in the systems, apparatuses, and methods disclosed herein may be made without departing from the scope of the instant disclosure, which is defined, at least in part, in the appended claims. The words "including" and "having," as used herein including the claims, shall have the same meaning as the word "comprising."

What is claimed is:

1. A method of evaluating a volume of superabrasive material, the method comprising;
    exposing the superabrasive material to radiation, wherein the superabrasive material includes a plurality of diamond grains defining a plurality of interstitial spaces, and wherein the superabrasive material includes a first region and a second region, the first region having a catalyst material disposed in at least some of the plurality of interstitial spaces in the amount of about 1 weight percent to about 7.5 weight percent of the superabrasive material, and wherein the second region is a catalyst diminished region;
    monitoring a reaction of the radiation to which the superabrasive material is exposed, wherein monitoring the reaction includes monitoring at least one of the group consisting of backscattered radiation and x-ray radiation; and
    determining a location of the boundary between the first region and the second region of the superabrasive volume in response to the monitored reaction of the radiation, the location of the boundary being approximately 500 µm or greater from a working surface of the volume superabrasive material.

2. The method according to claim 1, wherein determining a location of the boundary includes determining a location of a boundary that is approximately 600 µm or greater from the working surface.

3. The method according to claim 1, wherein determining a location of the boundary includes determining a location of a boundary that is approximately 700 µm or greater from the working surface.

4. The method according to claim 1, wherein determining a location of the boundary includes mapping a boundary that varies in its distance with respect to the working surface.

5. The method according to claim 1, wherein the second region comprises a second material among the interstices of the matrix material, the second material being different from the catalyst material.

6. The method according to claim 5, wherein the catalyst material comprises a solvent-metal catalyst.

7. The method according to claim 6, wherein the second material comprises copper.

8. The method according to claim 7, wherein the second material is a copper-tin alloy.

9. The method according to claim 6, wherein the second material comprises a carbide or cobalt.

10. The method according to claim 1, wherein exposing the superabrasive material to radiation comprises exposing the superabrasive material to beta particles.

11. The method according to claim 10, wherein monitoring a reaction of the radiation to which the superabrasive material is exposed comprises detecting a quantity of beta particles that are scattered when exposed to the superabrasive material.

12. The method according to claim 1, wherein the superabrasive material exhibits a coercivity of about 115 Oerstads (Oe) or more.

13. The method according to claim 12, wherein the superabrasive material exhibits a coercivity of about 115 Oe to about 175 Oe.

14. The method according to claim 12, wherein the diamond grains exhibit an average grain size of about 30 μm or less.

15. The method according to claim 1, wherein the superabrasive material exhibits a specific magnetic saturation of about 15 Gauss·cm$^3$/grams or less.

16. The method according to claim 1, wherein the superabrasive material exhibits a $G_{ratio}$ of at least about $4.0 \times 10^6$.

17. The method according to claim 1, wherein the the diamond grains exhibit an average grain size of about 30 μm or less.

18. A method of evaluating a volume of superabrasive material, the method comprising:

exposing the superabrasive material to radiation wherein the superabrasive material includes a plurality of diamond grains defining a plurality of interstitial spaces and a catalyst material disposed in at least some of the plurality of interstitial spaces, wherein the catalyst material is about 1 weight percent to about 7.5 weight percent of the superabrasive material;

monitoring a reaction of the radiation to which the superabrasive material is exposed, wherein monitoring the reaction includes monitoring at least one of the group consisting of backscattered radiation and x-ray fluorescence; and determining a location of the boundary between a first region and a second region of the superabrasive volume in response to the monitored reaction of the radiation, the location of the boundary being approximately 500 μm or greater from a working surface of the volume superabrasive material.

* * * * *